United States Patent
Nouri et al.

(10) Patent No.: US 12,094,378 B2
(45) Date of Patent: Sep. 17, 2024

(54) HEAD-MOUNTABLE DISPLAY (HMD) IMAGE AND FOVEAL REGION BRIGHTNESS COMPUTATION

(71) Applicant: Hewlett-Packard Development Company, L.P., Spring, TX (US)

(72) Inventors: Joseph Nouri, Fort Collins, CO (US); Kevin Smathers, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 18/005,348

(22) PCT Filed: Jul. 17, 2020

(86) PCT No.: PCT/US2020/042465
§ 371 (c)(1),
(2) Date: Jan. 12, 2023

(87) PCT Pub. No.: WO2022/015319
PCT Pub. Date: Jan. 20, 2022

(65) Prior Publication Data
US 2023/0282139 A1    Sep. 7, 2023

(51) Int. Cl.
G09G 3/00    (2006.01)
A61B 5/16    (2006.01)
G06F 3/01    (2006.01)

(52) U.S. Cl.
CPC ............ *G09G 3/003* (2013.01); *A61B 5/163* (2017.08); *G06F 3/013* (2013.01);
(Continued)

(58) Field of Classification Search
CPC ................ G02B 27/0101; G02B 30/22; G02B 2027/0112; G02B 2027/0118;
(Continued)

(56) References Cited

U.S. PATENT DOCUMENTS 6,252,989 B1    6/2001    Geisler et al.
9,087,471 B2    7/2015    Miao
(Continued)

FOREIGN PATENT DOCUMENTS

CN    110427108 A    11/2019
EP    1147900 A1    10/2001
(Continued)

OTHER PUBLICATIONS

Chen, S. et al, "Using Task-Induced Pupil Diameter and Blink Rate to Infer Cognitive Load", Human Computer Interaction, Apr. 29, 2014, pp. 1-31.
(Continued)

*Primary Examiner* — Nelson M Rosario
(74) *Attorney, Agent, or Firm* — Quarles & Brady LLP

(57) ABSTRACT

A computing device is configured to downsample an image that is displayable at a head-mountable display (HMD) to an image pixel representative of the image. The computing device computes a luminance of the image pixel from a color value of the image pixel to determine image brightness. The computing device is configured to determine the foveal region of the image from eye-tracking information of the user of the HMD. The computing device dowsamples the foveal region of the image to a foveal pixel representative of the foveal region. The computing device is configured to compute a luminance of the foveal pixel from a color value of the foveal pixel to determine foveal region brightness.

18 Claims, 5 Drawing Sheets

(52) U.S. Cl.
CPC ............... *G09G 2320/0666* (2013.01); *G09G 2320/0686* (2013.01); *G09G 2340/02* (2013.01); *G09G 2340/0407* (2013.01); *G09G 2354/00* (2013.01)

(58) Field of Classification Search
CPC ...... G02B 2027/014; G02B 2027/0187; G06F 3/011; G06F 3/013
See application file for complete search history.

(56) References Cited

U.S. PATENT DOCUMENTS

| | | | |
|---|---|---|---|
| 10,191,284 B2 | 1/2019 | Border et al. | |
| 10,345,590 B2 | 7/2019 | Samec et al. | |
| 11,009,944 B1* | 5/2021 | Choi | G09G 3/3275 |
| 11,227,449 B2* | 1/2022 | Breugelmans | G06T 11/40 |
| 2007/0003152 A1 | 1/2007 | Hoppe et al. | |
| 2015/0363978 A1 | 12/2015 | Maimone et al. | |
| 2016/0085302 A1 | 3/2016 | Publicover et al. | |
| 2017/0169602 A1 | 6/2017 | Blackmon et al. | |
| 2017/0336641 A1* | 11/2017 | von und zu Liechtenstein | G06T 19/006 |
| 2018/0308266 A1 | 10/2018 | Surti et al. | |
| 2019/0102936 A1 | 4/2019 | Neulander et al. | |
| 2019/0361233 A1 | 11/2019 | Ogawa | |
| 2020/0073143 A1 | 3/2020 | MacNamara et al. | |
| 2020/0143585 A1 | 5/2020 | Seiler et al. | |
| 2021/0329316 A1* | 10/2021 | Ninan | H04N 21/6547 |

FOREIGN PATENT DOCUMENTS

| | | |
|---|---|---|
| EP | 1308286 A1 | 5/2003 |
| EP | 1577108 A2 | 9/2005 |
| JP | 11-101935 A | 4/1999 |
| WO | 2020/018458 A1 | 1/2020 |

OTHER PUBLICATIONS

Gjoreski, M. et al., "Datasets for Cognitive Load Inference Using Wearable Sensors and Psychological Traits", Appl. Sci., May 31, 2020, vol. 10, Issue 11, pp. 1-20.

Novak, K. et al., "Assessment of cognitive load through biometric monitoring", 7th International Conference on Information Society and Technology ICIST, 2017, pp. 303-306.

* cited by examiner

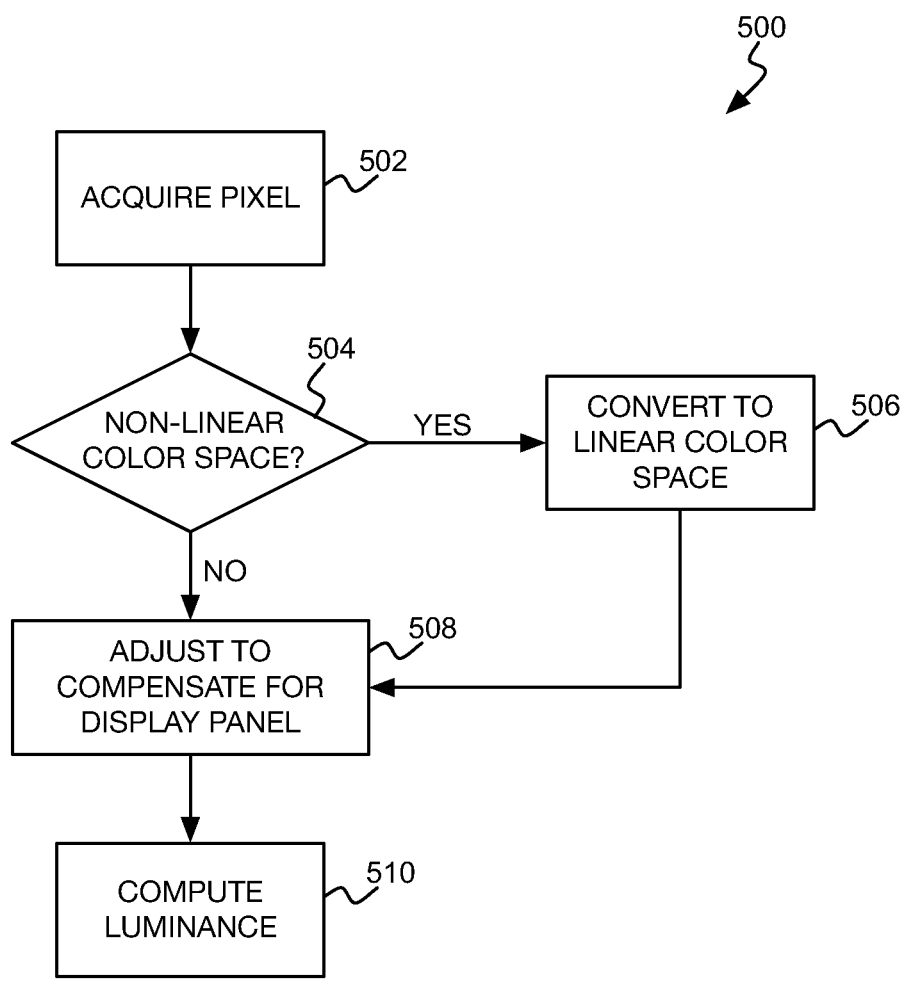

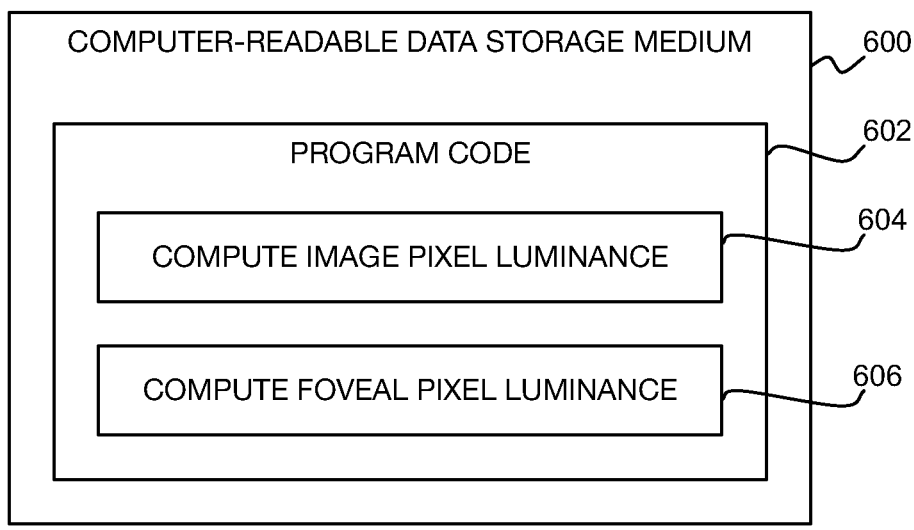
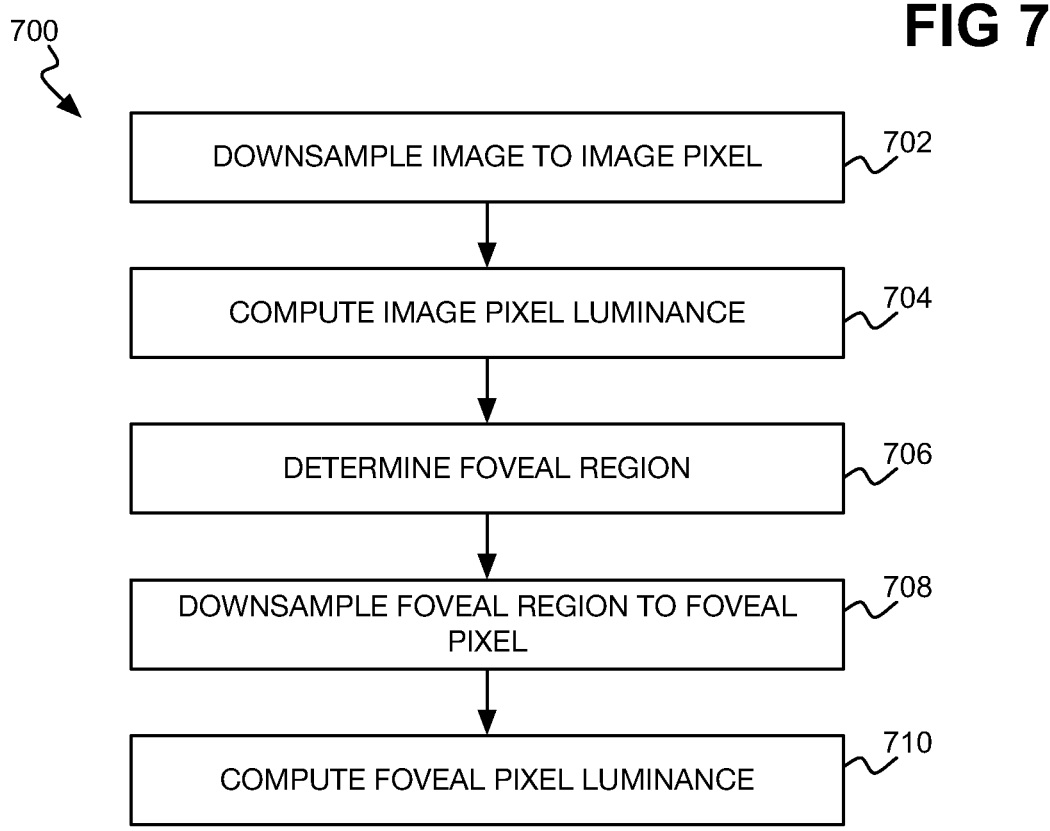

HEAD-MOUNTABLE DISPLAY (HMD) IMAGE AND FOVEAL REGION BRIGHTNESS COMPUTATION

BACKGROUND

Extended reality (XR) technologies include virtual reality (VR), augmented reality (AR), and mixed reality (MR) technologies, and quite literally extend the reality that users experience. XR technologies may employ head-mountable displays (HMDs). An HMD is a display device that can be worn on the head. In VR technologies, the HMD wearer is immersed in an entirely virtual world, whereas in AR technologies, the HMD wearer's direct or indirect view of the physical, real-world environment is augmented. In MR, or hybrid reality, technologies, the HMD wearer experiences the merging of real and virtual worlds.

BRIEF DESCRIPTION OF THE DRAWINGS

FIG. 5 is a flowchart of an example method for computing luminance of an image or foveal region from an image or foveal pixel, as the image or foveal region brightness.

FIG. 6 is a diagram of an example non-transitory computer-readable data storage medium.

FIG. 7 is a flowchart of an example method.

DETAILED DESCRIPTION

Figure 1:
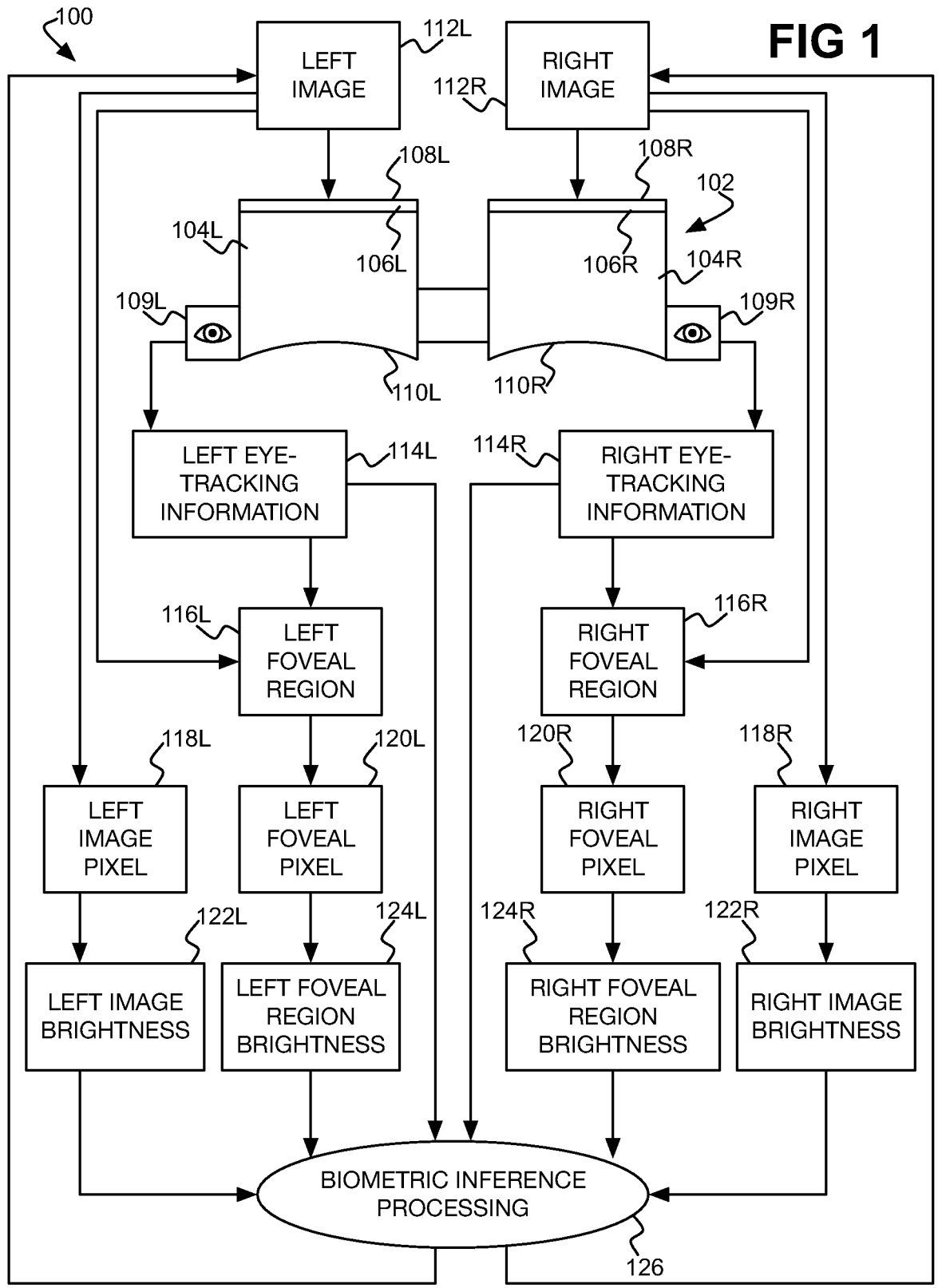
FIG. 1 is a diagram of an example topology for computing head-mountable display (HMD) image and foveal region brightness.

As noted in the background, a head-mountable display (HMD) can be employed as an extended reality (XR) technology to extend the reality experienced by the HMD's wearer. An HMD can include a small display panel in front of each eye of the wearer, as well as various sensors to detect or sense the wearer and/or the wearer's environment so that the images on the display panels convincingly immerse the wearer within an XR, be it a virtual reality (VR), augmented reality (AR), a mixed reality (MR), or another type of XR. An HMD may include a lens or multiple lenses positioned in the optical path between each display panel and the corresponding eye of the user.

An HMD can be employed as an adjunct to biometric inference processing, which is the analysis of biometric information of the wearer of the HMD in order to make an inference regarding the wearer's state. One type of such biometric inference processing is the estimation or gauging of cognitive load. The cognitive load of a user may be non-restrictively defined as a multidimensional construct representing the load that performing a particular task imposes on a user's cognitive system. Tasks may be objectively more or less demanding, people can have different cognitive capacities, and certain tasks may be easier for those who are skilled in the tasks.

Cognitive load can be gauged from pupillary variance, which lends itself well to estimation for the wearer of an HMD because eye-tracking information that the HMD ordinarily measures may include such pupillary metrics. However, to use pupillary variance as an accurate estimation of cognitive load, the effects of image and foveal region brightness have to first be removed or otherwise compensated for. This is because both image and foveal region brightness also affect pupillary variance, apart from the HMD wearer's cognitive load.

Image brightness is the brightness of the overall image displayed to and thus viewed by the eye. In the case in which the HMD is in the form of goggles or a helmet having eyecups adjacently positioned against the wearer's face during usage, the wearer's eyes are not exposed to light other than light from the HMD's panels that display the images. By comparison, in the case in which the HMD is in the form of glasses, the wearer's eyes may also be exposed to external or environmental ambient light.

The foveal region of an image may be estimated as the portion of the image at which the HMD wearer is gazing. More accurately, the foveal region is the portion of the displayed image that the light of which enters the pupil of the eye and is incident against the foveal region of the eye. The eye's foveal region resides at the inside back of the eye, where the eye is most sensitive to light. That is, the eye's foveal region is the part of the eye having the greatest cone density.

Techniques described herein provide ways by which image and foveal region brightness can be computed in realtime, without affecting image display at the HMD. For instance, image and foveal region brightness can be computed for each eye as eye-tracking information is refreshed and as the image displayed to each eye is refreshed. More specifically, image and foveal region brightness can be computed as the luminance of the image and the foveal region for each eye, as displayed at the HMD's display panels.

Four luminances can thus be computed: the luminance of an image and the luminance of the foveal region of that image for the left eye, and the luminance of an image and the luminance of the foveal region of that image for the right eye. Each luminance can accurately correspond to the actual measured luminance at the HMD if luminance were practically measurable in realtime. Such luminance contrasts with perceived luminance, which is the luminance perceived by the human perceptual system in the brain, and which may vary by person.

FIG. 1 shows an example topology 100 of the overall process by which left and right image and foveal region brightness can be computed in conjunction with an HMD 102. The HMD 102 includes left and right eyepiece assemblies 104L and 104R, which are collectively referred to as the eyepiece assemblies 104. The left and right eyepiece assemblies 104L and 104R have respective display panels 106L and 106R, collectively referred to as the display panels 106, at ends 108L and 108R opposite ends 110L and 110R at which the user of the HMD 102 positions his or her eyes. The display panels 106 may be flat-panel displays, such as liquid-crystal displays (LCDs) or light-emitting diode (LED) displays like organic LED (OLED) and microLED displays.

The HMD 102 further includes left and right eye-tracking sensors 109L and 109R, which are collectively referred to as the eye-tracking sensors 109. The eye-tracking sensors 109 track the gaze of the HMD user's eyes in relation to the display panels 108, and may include cameras and other types of hardware components, for instance. The HMD 102 can itself include other components, too, such as one or multiple various lenses in the optical path between the user's eyes at the ends 110L and 110R of the eyepiece assemblies 104 and the display panels 106 at the ends 108L and 108R of the assemblies 104.

Left and right images 112L and 112R, collectively referred to as the images 112, are respectively displayed at the display panels 108L and 108R. The images 112 are different from one another, but correspond to one another, so that upon the eyes simultaneously viewing the images 112 the brain of the HMD user stereoscopically perceives a single image. Left and right eye-tracking information 114L and 114R, collectively referred to as the eye-tracking information 114, is acquired from the HMD 102, on which basis the left and right foveal regions 116L and 116R of the images 112L and 112R can be estimably determined. The foveal regions 116L and 116R are collectively referred to as the foveal regions 116.

The left image 112L is downsampled or compressed to determine a left image pixel 118L representative of the image 112L, and the right image 112R is likewise downsampled or compressed to determine a right image pixel 118R representative of the image 112R. The image pixels 118L and 118R are collectively referred to as the image pixels 118. Each image pixel 118 is representative of its respective image 112 in that an image pixel 118 has a color value that is an average of the color values of the respective image 112's constituent pixels. A color value may be expressed as a tuple of three color values, such as red, green, and blue values.

Similarly, the left foveal region 116L is downsampled or compressed to determine a left foveal pixel 120L representative of the foveal region 116L of the left image 112L, and the right foveal region 116R is likewise downsampled or compressed to determine a right foveal pixel 120R representative of the foveal region 116R of the right image 112R. The foveal pixels 120L and 120R are collectively referred to as the foveal pixels 120. Each foveal pixel 120 is representative of its respective foveal region 116 in that a foveal pixel 120 has a color value that is an average of the color values of the pixels of the respective foveal region 116 of the image 112 in question.

The left image brightness 122L and the right image brightness 122R are respectively computed from the left image pixel 118L and the right image pixel 118R. The left and right image brightnesses 122L and 122R are collectively referred to as the image brightnesses 122. Each image brightness 122 represents the overall brightness of its respective image 112, and may be determined as the luminance of its respective image pixel 118, from the color value of this pixel 118.

Similarly, the left foveal region brightness 124L and the right foveal region brightness 124R are respectively computed from the left foveal pixel 120L and the right foveal pixel 120R. The left and right foveal region brightnesses 124L and 124R are collectively referred to as the foveal region brightnesses 124. Each foveal region brightness 124 represents the overall brightness of its respective foveal region 116 of the image 112 in question, and may be determined as the luminance of its respective foveal pixel 120, from the color value of this pixel 120.

Biometric inference processing 126 may be performed based on the image brightnesses 122 and the foveal region brightnesses 124, as well as other information. For instance, the eye-tracking information 114 may include pupillary variance (e.g., pupil diameter variance) of each eye of the HMD user, from which the effects of the brightnesses 122 and 124 are removed or otherwise compensated for. As noted, the biometric inference processing 126 can include gauging or estimating cognitive load of the HMD user.

In one implementation, the images 112 displayed by the HMD 102 to the user can be adjusted based on the results of the biometric inference processing 126. As one example, the HMD user may be performing a task on a machine by following instructions presented at the HMD 102. Based on the estimated cognitive load of the HMD user in performing the task as well as other information, such as how well or correctly the user is performing the task, the instructions may be simplified or presented in more detail. The likelihood that the HMD user will make a mistake may even be predicted prior to the mistake actually occurring.

The biometric inference processing 126 and the resulting adjustment of the displayed images 126 can be performed by application software external to and separate from the program code that determines the brightnesses 122 and 124. That is, the biometric inference processing 126 that is performed and how the displayed images 112 are adjusted based on the inference processing 126 use the determined brightnesses 122 and 124, but the techniques for determining the brightnesses 122 and 124 described herein are independent of the such inference processing 126 and the images 126 adjustment. Such inference processing 126 and displayed image 126 adjustment may occur in realtime with or offline from the determination of the brightnesses 122 and 124.

Figure 2:
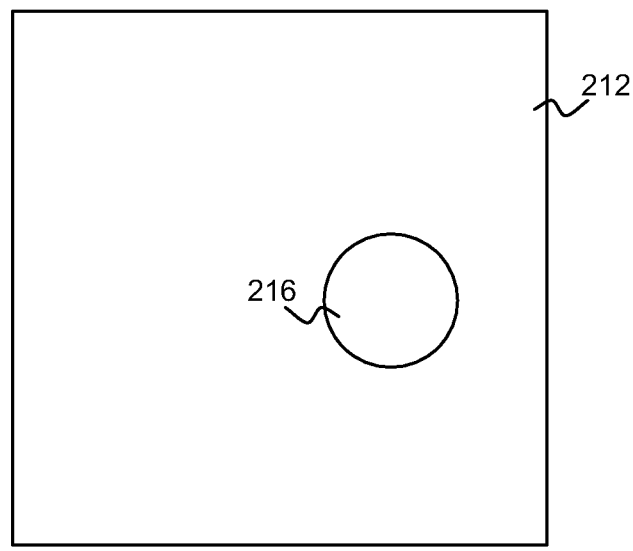
FIG. 2 is a diagram of an example image and foveal region thereof.

FIG. 2 shows an example image 212 in relation to which a foveal region 216 thereof is identified. The image 212 may be the left image displayed to the left eye of the HMD user or the right image displayed to the right eye of the HMD user. The foveal region 216 is the portion of the image 212 at which the user's gaze is directed, which can be determined from eye-tracking information captured by the HMD. As the user directs his or her focal attention to different parts of the image 212, the foveal region 216 accordingly changes.

Figure 3:
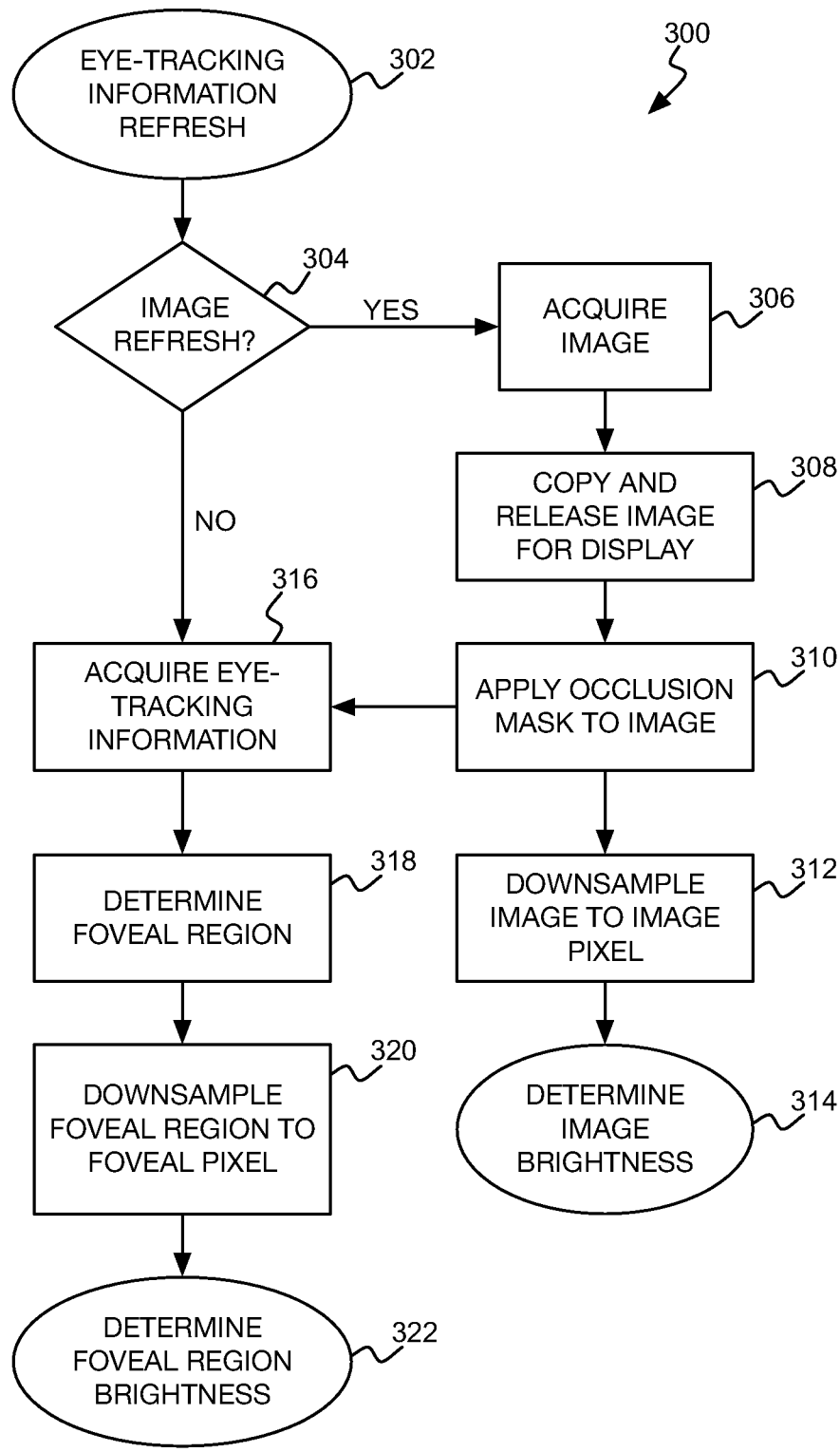
FIG. 3 is a flowchart of an example method for determining an image pixel representative of an image and a foveal pixel representative of a foveal region of the image.

FIG. 3 shows an example method 300 for determining an image pixel representative of an image and a foveal pixel representative of a foveal region of the image. The method 300 is described in relation to one such image, but is performed for each of the left image displayed to the HMD user's left eye and the right image displayed to the HMD user's right eye. The method 300 can be performed by a host computing device to which the HMD is communicatively connected, such as a desktop or laptop computer or a mobile computing device like a smartphone or tablet computing device. The method 300 may be implemented as program code stored on a non-transitory computer-readable data storage medium and executable by a processor of a host computing device.

In one implementation, the method 300 is performed by a graphics processor unit (GPU) of the host computing device, as opposed to a different processor like a central processor unit (CPU) of the device. The method 300 is specifically shown in the example of FIG. 3 for such an implementation, and leverages the processing capabilities that may be unique to a GPU (as compared to a CPU) to permit image and foveal pixel determination (and thus image and foveal region brightness) in real-time, without slowing the display of the image at the HMD. By comparison, performing such processing at the CPU may unduly burden the CPU, and may not permit real-time determination of image and foveal pixels.

The method 300 is described in relation to an example in which the refresh rate at which eye-tracking information is updated is faster than the refresh rate at which the image displayed at the HMD is updated. In such an example, the method 300 is repeated at every refresh of the eye-tracking information, for both the left and right eye. At a refresh of the eye-tracking information (302), the image to be displayed at the HMD may or may not have been refreshed since the last refresh of the eye-tracking information refresh. If image refresh has occurred (304), the method 300 includes then acquiring the image (306), such as from a compositor that generates the image for display.

The method 300 includes copying and releasing the image for display at the display panel of the HMD (308). For instance, the image may be bit block transferred (i.e., bit blitted, or blitted) from one region of a GPU's memory to another region. Blitting is performed very quickly. The remainder of the method 300 acts on the blitted copy of the image. The original image can thus be released for display at the display panel, without having to wait for completion of the method 300. As such, the display of the image at the HMD is not slowed, since blitting can be performed at speeds much faster than image refresh rates in practice.

The method 300 may include applying an occlusion mask to the image (310). Although the image may be perfectly rectangular or square, the physical geometry of the HMD or its current physical configuration may cause occlusion of portions of the image. The eye of the HMD user is not exposed to the occluded image portions, and therefore these portions are not considered when determining overall image brightness. The occlusion mask defines which portions of the image are visible and which are occluded, and application of the mask removes the occluded portions from the image. In another implementation, however, no occlusion may occur at the HMD, or the image acquired in part 306 may already account for occlusion, in which case occlusion mask has to be applied.

The method 300 includes then downsampling the image to an image pixel representative of the image (312). As noted, the downsampled image pixel has a color value that is an average of the color values of the image's constituent images. A GPU is in particular well suited for such downsampling because it can perform mipmapping. Mipmapping is the process of progressively downsampling an image by orders of two, which can culminate in a one pixel-by-one pixel mipmap of the image that can correspond to the determined image pixel. The downsampling process may also be referred to as a compression process, since the GPU may recursively perform wavelet or other compression on the image to realize the one pixel-by-one pixel mipmap. Example image downsampling is illustratively described later in the detailed description.

Brightness of the image can then be determined based on the image pixel (314). A particular manner by which image brightness is computed from the determined image pixel is described later in the detailed description. Image brightness computation may be performed at the CPU of the host computing device, or at the GPU of the host computing device. For instance, the calculations performed to compute image brightness from the image pixel may be better suited for the processing capabilities of a CPU as compared to those of a GPU, thus lending itself to performance by the CPU both to calculate the image brightness in realtime with the display of the image at the HMD and to avoid unnecessary burdening of the GPU.

As to foveal region brightness determination, the method 300 includes acquiring eye-tracking information from the HMD (316). The method 300 includes then determining the foveal region of the image displayed at the HMD using the acquired eye-tracking information (318). If at eye-tracking information refresh the image was refreshed since the last refresh of the eye-tracking information, then the foveal region is determined for the image acquired in part 306 in the current iteration of the method 300. By comparison, if at eye-tracking information refresh the image was not refreshed since the last refresh of the eye-tracking information, then the foveal region is determined for the image acquired in part 306 in the previous iteration of the method 300.

The eye-tracking information may specify a vector extending outwards in three-dimensional space from the center of the HMD user's eye pupil towards the display panel of the HMD at which the image is displayed. Determining the foveal region of the image can thus entail projecting the three-dimensional vector onto a two-dimensional surface representative of the display panel. The foveal region is a contiguous portion of the image as a whole. As noted, the foveal region is the portion of the image at which the user's gaze is directed, as an estimation of the portion of the image that is incident upon the foveal region of the user's eye.

The method 300 includes then downsampling the foveal region of the image to a foveal pixel representative of the foveal region (320). Downsampling the foveal region is performed in the same manner as image downsampling, but starting with the foveal region of the image instead of the image as a whole. Once the foveal region has been downsampled or compressed to a foveal pixel, foveal region brightness can be determined based on the foveal pixel (322), in the same manner in which image brightness is determined from the image pixel.

As noted, FIG. 3 shows an example implementation of the method 300 in which eye-tracking information is refreshed more quickly than the image displayed at the HMD. However, in another implementation, the image refresh rate may be faster than the rate at which the eye-tracking information is refreshed. In this case, performance of the method 300 is predicated on image refresh, and thus the method 300 is repeated each time the image is refreshed. Even though the eye-tracking information may not have refreshed, the foveal region is determined with each iteration of the method 300 because the image of which the foveal region is a part will have changed.

Figure 4:
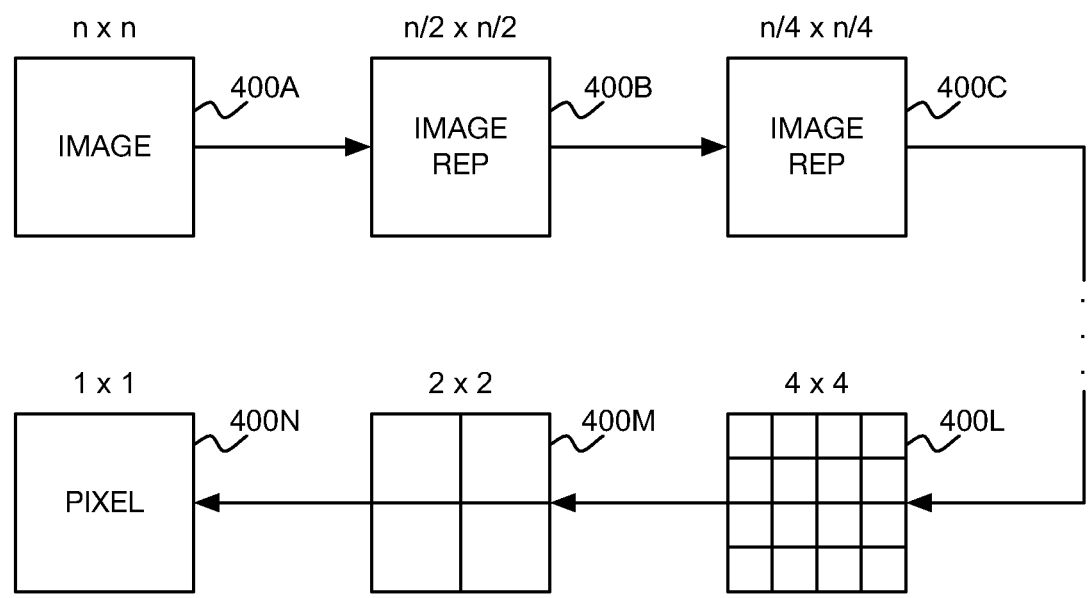
FIG. 4 is a diagram of example downsampling of an image or foveal region to a representative image or foveal pixel.

FIG. 4 shows example downsampling of an image to an image pixel, as may be performed by a GPU of a host computing device in part 312 of FIG. 3. The downsampling process starts with an image, which may have a resolution of n pixels by n pixels. (Downsampling a foveal region of an image to a foveal pixel, such as in part 318, is performed in the same way, but starts with the foveal region of an image, instead of the image in its entirety.) The image may be considered an initial image representation 400A at full n pixels-by-n pixels resolution.

The image representation 400A is downsampled by an order of two to an image representation 400B having a resolution of n/2 pixels by n/2 pixels. The image representation 400B is then downsampled by an order of two to an image representation 400C having a resolution of n/4 pixels by n/4 pixels. Such downsampling or compression is successively repeated, resulting in a four pixel-by-four pixel image representation 400L and then a two pixel-by-two pixel image representation 400M before culminating in a compressed one pixel-by-one pixel image representation 400N, which is a single image pixel representative of the entire image.

The image representations 400A, 400B, 400C, . . . , 400L, 400M, and 400N are collectively referred to as the image representations 400. The image representations other than the first image representation 400A may be progressive mipmaps of reduced resolution by orders of two, which are computed by a GPU using its mipmapping functionality. A mipmap is a lower representation of an image, namely the image corresponding to the initial image representation 400A.

As noted, the image pixel (i.e., the one pixel-by-one pixel image representation 400N) is representative of the image as a whole, and has a color value that is the average color value of the image's constituent n-by-n pixels. Brightness of the image as a whole can be determined from this image pixel. However, in another implementation, there may be more than one image pixel for which image brightness is determined. For example, image brightness may be determined for each image pixel of the two pixel-by-two pixel image representation 400M.

In this case, the upper-left image pixel of the image representation 400M has a color value that is the average color value of the corresponding upper-left quadrant of constituent pixels of the image. Similarly, the upper-right, lower-right, and lower-left image pixels of the image representation 400M have color values that are the average color values of the corresponding upper-right, lower-right, and lower-left quadrants of the pixels of the image, respectively. Determining image brightness for more than one image pixel (and, similarly, foveal region brightness for more than one foveal pixel) may be beneficial if pupillary variation is not uniformly affected by brightness.

An image can be downsampled to a pixel using approaches other than mipmapping. For example, compute shaders that do not use mipmaps can be used. Compute shaders are computer programs (e.g., programmable stages, including vertex and geometry stages) executed by GPUs that instances of which can be concurrently performed by corresponding hardware processing units of the GPUs. An example of such hardware processing units are single instruction-multiple data (SIMD) units, for instance.

FIG. 5 shows an example method 500 for computing luminance of an image or foveal region from an image or foveal pixel. The computed image luminance corresponds to and serves as the determined brightness of the image, and likewise the computed foveal region luminance corresponds to and serves as the determined brightness of the foveal region. The method 500 can thus be performed to realize parts 314 and 322 of FIG. 3. The method 500 is described in relation to computing image luminance, but is equally applicable to computing foveal region luminance.

The method 500 can be performed by the host computing device to which the HMD is communicatively connected. Like the method 300, the method 500 may be implemented as program code stored on a non-transitory computer-readable data storage medium and executable by a processor of the host computing device. As noted, image brightness may be more suitably determined by a CPU of the host computing device instead of by the device's GPU, such that the method 500 may accordingly be performed by the CPU.

The method 500 includes acquiring the image pixel (512). For example, the CPU of the host computing device may read the image pixel that the GPU determined. The color space of the image, and thus the color values of the image pixel, may be in a linear color space or a non-linear color space. If the color space is non-linear (504), then the method 500 includes converting the color values to a linear color space (506) so that luminance of the image pixel is properly computed. The red-green-blue (RGB) color space is an example of a linear color space, whereas the standard RGB (sRGB) color space is an example of a non-linear color space.

The method 500 can include adjusting the image pixel to compensate for the HMD display panel at which the image is displayed (508). More specifically, the color values of the image pixel are adjusted to compensate for brightness variations characteristic of the display panel in displaying different colors. The color values of the image pixel may thus be adjusted using an experimentally derived look-up table (LUT), or in another manner, to compensate for such variations. Different characteristics of the display panel may cause these brightness variations.

For instance, a physical pixel of the display panel may be made up of red, green, and blue sub-pixels, some of which may be shared with adjacent physical pixels of the panel. Whereas an ideal display panel displays each sub-pixel color at uniform brightness, in actuality some colors may be brighter or dimmer than other colors. The number of physical sub-pixel elements, such as LCD cells or LEDs, corresponding to each sub-pixel color may vary. The physical arrangement of the sub-pixel elements in forming a sub-pixel may differ for different colors of the same display panel and for different panels.

The method 500 concludes with computing the luminance of the image pixel from the color values of the pixel (510). Because the color values are for a linear color space, the luminance may be calculated using an equation. For instance, for the RGB color space, the luminance may be calculated as the maximum value of the red, green, and blue color values. As another example, the luminance may be this maximum value minus the minimum value of the red, green, and blue color values, with the resulting difference divided by two. As noted, the computed luminance serves as the brightness of the image. The method 500 is performed for both left image brightness and right image brightness, as well as for both left foveal region brightness and right foveal region brightness. If more than one pixel is determined for each image and each foveal region, then the method 500 is likewise performed for each image pixel and each foveal region.

FIG. 6 shows an example non-transitory computer-readable data storage medium 600 storing program code 602. The program code 602 is executable by a computing device, such as a host computing device connected to an HMD, to perform processing. The processing includes computing a luminance an image pixel representative of an image displayable at the HMD from a color value of the image pixel to determine image brightness (604). The processing includes computing a luminance of a foveal pixel representative of a foveal region of the image from a color value of the foveal pixel to determine foveal region brightness (606). The foveal region is determined from eye-tracking information of a user of the HMD.

FIG. 7 shows an example method 700, which can be performed by a computing device like a host computing device connected to an HMD. The method 700 includes downsampling an image displayable at a HMD to an image pixel representative of the image (702), and computing a luminance of the image pixel from a color value of the image pixel to determine image brightness (704). The method 700 includes determining a foveal region of the image from eye-tracking information of a user of the HMD (706). The method 700 includes downsampling the foveal region of the image to a foveal pixel representative of the foveal region of the image (708), and computing a luminance of the foveal pixel from a color value of the foveal pixel to determine foveal region brightness (710).

Techniques have been described from determining image and foveal region brightness in realtime as images are displayed at an HMD. The image and foveal region brightness are determined as image and foveal region luminance computed from image and foveal pixels representative of the image and foveal region, respectively. The determined image and foveal region brightness can be used when performing biometric inference processing regarding the user of the HMD.

We claim:

1. A method comprising:
   downsampling, by a computing device, an image displayable at a head-mountable display (HMD) to an image pixel representative of the image;
   computing, by the computing device, a luminance of the image pixel from a color value of the image pixel, to determine image brightness;
   determining, by the computing device, a foveal region of the image from eye-tracking information of a user of the HMD;
   downsampling, by the computing device, the foveal region of the image to a foveal pixel representative of the foveal region of the image; and
   computing, by the computing device, a luminance of the foveal pixel from a color value of the foveal pixel, to determine foveal region brightness,
   wherein the image is downsampled by mipmapping the image to a one pixel-by-one pixel mipmap as the image pixel, and
   wherein the foveal region of the image is downsampled by mipmapping the image to a one pixel-by-one pixel mipmap as the foveal pixel.

2. The method of claim 1, wherein the image is a left-eye image, the foveal region is a left-eye foveal region, the image brightness is a left-eye image brightness, and the foveal region brightness is a left-eye foveal region brightness,
   and wherein the method is repeated to determine a right-eye image brightness for a right-eye image and a right-eye foveal region brightness for a right-eye foveal region of the right-eye image.

3. The method of claim 1, where the computed image and foveal region brightnesses are removed in assessing pupil diameter variance during biometric inference processing regarding the user of the HMD.

4. The method of claim 3, wherein the biometric inference processing comprises gauging cognitive load of the user of the HMD.

5. The method of claim 3, wherein the image displayable at the HMD is adjusted based on the biometric inference processing regarding the user of the HMD.

6. The method of claim 1, wherein the eye-tracking information has a greater refresh rate than the image, and the method is repeated at every refresh of the eye-tracking information,
   and wherein the image is downsampled and the image brightness is determined at every refresh of the eye-tracking information if the image has been refreshed since a prior refresh of the eye-tracking information.

7. The method of claim 1, wherein the image has a greater refresh rate than the eye-tracking information, and the method is repeated at every refresh of the image.

8. The method of claim 1, wherein the image pixel is a selected image pixel, the image is downsampled by mipmapping the image to an n pixel-by-n pixel mipmap of a plurality of image pixels including the selected image pixel, and a luminance of each image pixel is computed,
   wherein the foveal pixel is a selected foveal pixel, the image is downsampled by mipmapping the foveal region of the image to an n pixel-by-n pixel mipmap of a plurality of foveal pixels including the selected foveal image pixel, and a luminance of each foveal pixel is computed.

9. The method of claim 1, wherein the eye-tracking information comprises a three-dimensional vector radiating outwards from an eye of the user in a gaze direction towards a display panel of the HMD at which the image is displayed,
   and wherein the foveal region is determined by projecting the three-dimensional vector onto a two-dimensional surface representative of the display panel.

10. The method of claim 1, wherein the image is displayed at the HMD in an occlusive manner, the method further comprising:
    prior to downsampling the image, applying, by the computing device, an occlusion mask to the image corresponding occluded portions of the image when displayed at the HMD.

11. The method of claim 1, wherein a display panel of the HMD at which the image is displayed has varying brightness characteristics for different sub-pixel colors, the method further comprising:
    prior to determining the luminance of the image pixel from the color value of the image pixel, adjusting, by the computing device, the color value of the image pixel to compensate for the varying brightness characteristics of the display panel for the different sub-pixel colors; and
    prior to determining the luminance of the foveal pixel from the color value of the foveal pixel, adjusting, by the computing device, the color value of the foveal pixel to compensate for the varying brightness characteristics of the display panel for the different sub-pixel colors.

12. A non-transitory computer-readable data storage medium storing program code executable by a computing device to perform processing comprising:
    downsampling an image displayable at a head-mountable display (HMD) to an image pixel representative of the image;
    computing a luminance of the image pixel representative of the image displayable at the HMD from a color value of the image pixel to determine image brightness;
    downsampling a foveal region of the image to a foveal pixel representative of the foveal region of the image; and
    computing a luminance of the foveal pixel representative of the foveal region of the image from a color value of the foveal pixel to determine foveal region brightness, the foveal region determined from eye-tracking information of a user of the HMD,
    wherein the image pixel is a selected image pixel, the image is downsampled by mipmapping the image to an n pixel-by-n pixel mipmap of a plurality of image pixels including the selected image pixel, and a luminance of each image pixel is computed, and
    wherein the foveal pixel is a selected foveal pixel, the image is downsampled by mipmapping the foveal region of the image to an n pixel-by-n pixel mipmap of a plurality of foveal pixels including the selected foveal pixel, and a luminance of each foveal pixel is computed.

13. The non-transitory computer-readable data storage medium of claim 12, wherein the processing further comprises:
  determining the image pixel by successively downsampling the image by an order of two at a graphics processing unit (GPU) of the computing device to yield a compressed image representation comprising the image pixel; and
  determining the foveal pixel by successively downsampling the image by an order of two at the GPU of the computing device to yield a compressed foveal region representation comprising the foveal pixel.

14. The non-transitory computer-readable data storage medium of claim 13, wherein the luminances of the image and foveal pixels are computed at a central processing unit (CPU) of the computing device.

15. A system comprising:
  head-mountable display (HMD);
  a processor to:
    downsample an image displayable at the HMD to an image pixel representative of the image;
    compute a luminance of the image pixel from a color value of the image pixel, to determine image brightness;
    determine a foveal region of the image from eye-tracking information of a user of the HMD;
    downsample the foveal region of the image to a foveal pixel representative of the foveal region of the image; and
    compute a luminance of the foveal pixel from a color value of the foveal pixel, to determine foveal region brightness,
  wherein a display panel of the HMD at which the image is displayed has varying brightness characteristics for different sub-pixel colors, the processor further to:
    adjust the color value of the image pixel to compensate for the varying brightness characteristics of the display panel for the different sub-pixel colors, prior to determining the luminance of the image pixel from the color value of the image pixel; and
    adjust the color value of the foveal pixel to compensate for the varying brightness characteristics of the display panel for the different sub-pixel colors, prior to determining the luminance of the foveal pixel from the color value of the foveal pixel.

16. The system of claim 15, wherein the image pixel is a selected image pixel, the image is downsampled by mipmapping the image to an n pixel-by-n pixel mipmap of a plurality of image pixels including the selected image pixel, and a luminance of each image pixel is computed,
  wherein the foveal pixel is a selected foveal pixel, the image is downsampled by mipmapping the foveal region of the image to an n pixel-by-n pixel mipmap of a plurality of foveal pixels including the selected foveal image pixel, and a luminance of each foveal pixel is computed.

17. The system of claim 15, wherein the image pixel is a two pixel-by-two pixel image representation.

18. The system of claim 15, wherein the eye-tracking information specifies a vector extending outwards in three-dimensional space from a center of a pupil of the user towards a display panel of the HMD at which the image is displayed.

* * * * *